United States Patent
Jordan et al.

(10) Patent No.: US 7,313,437 B2
(45) Date of Patent: Dec. 25, 2007

(54) ADAPTIVE DIASTOLIC INTERVAL CONTROL OF ACTION POTENTIAL DURATION ALTERNANS

(75) Inventors: Peter Nicholas Jordan, New York, NY (US); David Jon Christini, Brooklyn, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 322 days.

(21) Appl. No.: 11/064,793

(22) Filed: Feb. 24, 2005

(65) Prior Publication Data

US 2005/0192641 A1    Sep. 1, 2005

Related U.S. Application Data

(60) Provisional application No. 60/548,714, filed on Feb. 27, 2004.

(51) Int. Cl.
*A61N 1/00* (2006.01)
(52) U.S. Cl. ............................................. 607/9
(58) Field of Classification Search ............... 607/9; 128/898
See application file for complete search history.

(56) References Cited

U.S. PATENT DOCUMENTS

| | | | | |
|---|---|---|---|---|
| 5,555,889 A | * | 9/1996 | Karagueuzian et al. | 600/518 |
| 5,645,575 A | * | 7/1997 | Stangl et al. | 607/17 |
| 6,466,819 B1 | * | 10/2002 | Weiss | 607/5 |
| 6,920,353 B1 | * | 7/2005 | Heinze et al. | 607/5 |
| 6,993,388 B2 | * | 1/2006 | Bullinga | 607/9 |
| 7,047,067 B2 | * | 5/2006 | Gray et al. | 600/516 |
| 7,123,953 B2 | * | 10/2006 | Starobin et al. | 600/516 |
| 7,177,683 B2 | * | 2/2007 | Belk | 607/14 |
| 2004/0098061 A1 | * | 5/2004 | Armoundas et al. | 607/17 |
| 2004/0220640 A1 | * | 11/2004 | Burnes et al. | 607/28 |

FOREIGN PATENT DOCUMENTS

| DE | 10132228 C1 | * | 4/2003 |
|---|---|---|---|
| WO | WO 3002195 A2 | * | 1/2003 |

OTHER PUBLICATIONS

Christini, D.J., and J.J. Collins. 1995. Using Noise and Chaos Control to Control Nonchaotic Systems. Phys. Rev. E 52:5806-5809.
Christini, D.J., K.M. Stein, S.M. Markowitz, S. Mittal, D.J. Slotwiner, and B.B. Lerman. 1999. The Role of Nonlinear Dynamics in Cardiac Arrhythmia Control. Heart Disease 1:190-200.

(Continued)

*Primary Examiner*—George Manuel
*Assistant Examiner*—Christopher A. Flory
(74) *Attorney, Agent, or Firm*—Darby & Darby P.C.

(57) ABSTRACT

A real-time detection technique and a real-time, adaptive, model-independent control technique for detecting and stabilizing pathological physiological rhythms, such as repolarization alternans, on the basis of the rate dependence of excitable tissue such as cardiac and neuronal tissue is presented. Unlike other control methods, which require a number of beats to locate the period-1 fixed point, the technique locates the period-1 fixed point almost instantaneously, rapidly eliminating any higher-period or aperiodic rhythms.

19 Claims, 11 Drawing Sheets

OTHER PUBLICATIONS

Christini, D.J., K.M. Stein, S.M. Markowitz, S. Mittal, D.J. Slotwiner, M.A. Scheiner, S. Iwai, and B.B. Lerman. 2001. Nonlinear-Dynamical Arrhythmia Control in Humans. Proc. Natl. Acad. Sci. USA 98:5827-5832.

Echebarria, B., and A. Karma. 2002. Spatiotemporal Control of Cardiac Alternans. Chaos. 12:923-930.

Gauthier, D.J., and J.E.S. Socolar. 1997. Comment on Dynamic Control of Cardiac Alternans. Phys. Rev. Lett. 79:4938.

Gauthier, D.J., S. Bahar, and G.M. Hall. 2001. Controlling the Dynamics of Cardiac Muscle Using Small Electrical Stimuli. In Handbook of Biological Physics vol. 4: Neuro-Informatics and Neural Modeling. F. Moss and S. Gielen, editors. Elsevier/North Holland, Amsterdam. 229-255.

Hall, G.M., and D.J. Gauthier. 2002. Experimental Control of Cardiac Muscle Alternans. Phys. Rev. Lett. 88:198102.

Hall, K., and D.J. Christini. 2000. Restricted Feedback Control of One-Dimensional Maps. Phys. Rev. E 63:046204.

Hall, K., D.J. Christini, M. Tremblay, J.J. Collins, L. Glass, and J. Billette. 1997. Dynamic Control of Cardiac Alternans. Phys. Rev. Lett. 78:4518-4521.

Koller, M.L., M.L. Riccio, and R.F. Gilmour Jr. 1998. Dynamic Restitution of Action Potential Duration During Electrical Alternans and Ventricular Fibrillation. Am. J. Physiol. (Heart Circ. Physiol.) 275:H1635-H642.

Luo, C.-H., and Y. Rudy. 1991. A Model of the Ventricular Cardiac Action Potential: Depolarization, Repolarization, and Their Interaction. Circ. Res. 68:1501-1526.

Noble, D. 1962. A Modification of the Hodgkin-Huxley Equations Applicable to Purkinje Fiber Action and Pace-Maker Potential. J. Physiol. 160:317-352.

Ott, E., C. Grebogi, and J.A. Yorke. 1990. Controlling Chaos. Phys. Rev. Lett. 64:1196-1199.

Pastore, J.M., S.D. Girouard, K.R. Laurita, F.G. Akar, and D.S. Rosenbaum. 1999. Mechanism Linking T-Wave Alternans to the Genesis of Cardiac Fibrillation. Circulation 99:1385-1394.

Qu, Z., A. Garfinkel, P.-S. Chen, and J.N. Weiss. 2000. Mechanisms of Discordant Alternans and Induction of Reentry in Simulated Cardiac Tissue. Circulation 102:1664-1670.

Sukow, D.W., M.E. Bleich, D.J. Gauthier, and J.E.S. Socolar. 1997. Controlling Chaos in a Fast Diode Resonator Using Extended Time-Delay Autosynchronization: Experimental Observations and Theoretical Analysis. Chaos 7:560-576.

Tachibana, H., I. Kubota, M. Yamaki, T. Watanabe, and H. Tomoike. 1998. Discordant S-T Alternans Contributes to Formation of Reentry: a Possible Mechanism of Reperfusion Arrhythmia Am. J. Physiol. (Heart Circ. Physiol.) 275:H116-H121.

Watanabe, M., and R.F. Gilmour Jr. 1996. Strategy for Control of Complex Low-Dimensional Dynamics in Cardiac Tissue. J. Math. Biol. 35:73-87.

Watanabe, M.A., F.H. Fenton, S.J. Evans, H.M. Hastings, and A. Karma. 2001. Mechanisms for Discordant Alternans. J. Cardiovasc. Electrophysiol. 12:196-206.

Zaniboni, M., A.E. Pollard, L. Yang, and K.W. Spitzer. 2000. Beat-to-Beat Repolarization Variability in Ventricular Myocytes and Its Suppression by Electrical Coupling. Am. J. Physiol. (Heart Circ. Physiol.) 278:H677-H687.

A. Patwardhan, S. Moghe 2001. Novel Feedback Based Stimulation Protocol Shows Hysteresis in Cardiac Action Poetential Duration Restitution Biomedical Sciences Instrumentation (Instrument Society of America) 37:505-510.

R. Wu, A. Patwardhan 2004. Restitution of Action Potential Duration During Sequential Changes in Diastolic Intervals Shows Multimodal Behavior American Heart Association, Inc. 634-641.

D.J. Christini, J.J. Collins 1997 Real-Time, Adaptive, Model-Independent Control of Low-Dimensional Chaotic and Nonchaotic Dynamical Systems IEEE Fundamental Theory and Applications, vol. 44, No. 10; 1027-1029.

Cao, J.-M., Z Qu, Y.-H.Kim, T.-J.Wu, A. Garfinkel, J.N. Weiss, H.S. Karagueuzian, and P.-S. Chen. 1999. Spatiotemporal Heterogeneity in the Induction of Ventricular Fibrillation by Rapid Pacing: Importance of Cardiac Resitution Properties. Circ. Res. 1318-1331.

Boyett, M.R., and B.R. Jewell. 1980. Analysis Of The Effects Of Changes In Rate And Rhythm Upon Electrical Activity In The Heart. Prog. Biophys. Mol. Biol. 36:1-52.

Christini, D.J., and J.J. Collins. 1997b. Control Of Chaos In Excitable Physiological Systems: A Geometric Analysis. Chaos 7:544-549.

Elharrar, V., and B. Surawicz. 1983. Cycle Length Effect On Restitution Of Action Potential Duration In Dog Cardiac Fibers. Am. J. Physiol. (Heart Circ. Physiol.) 244:H782-H792.

Garfinkel, A., M.L. Spano, W.L. Ditto, and J.N. Weiss. 1992. Controlling Cardiac Chaos. Science 257:1230-1235.

Sauer, T. 1997. Reconstruction Of Integrate-And-Fire Dynamics. Fields Inst. Commun. 11:63-75.

* cited by examiner

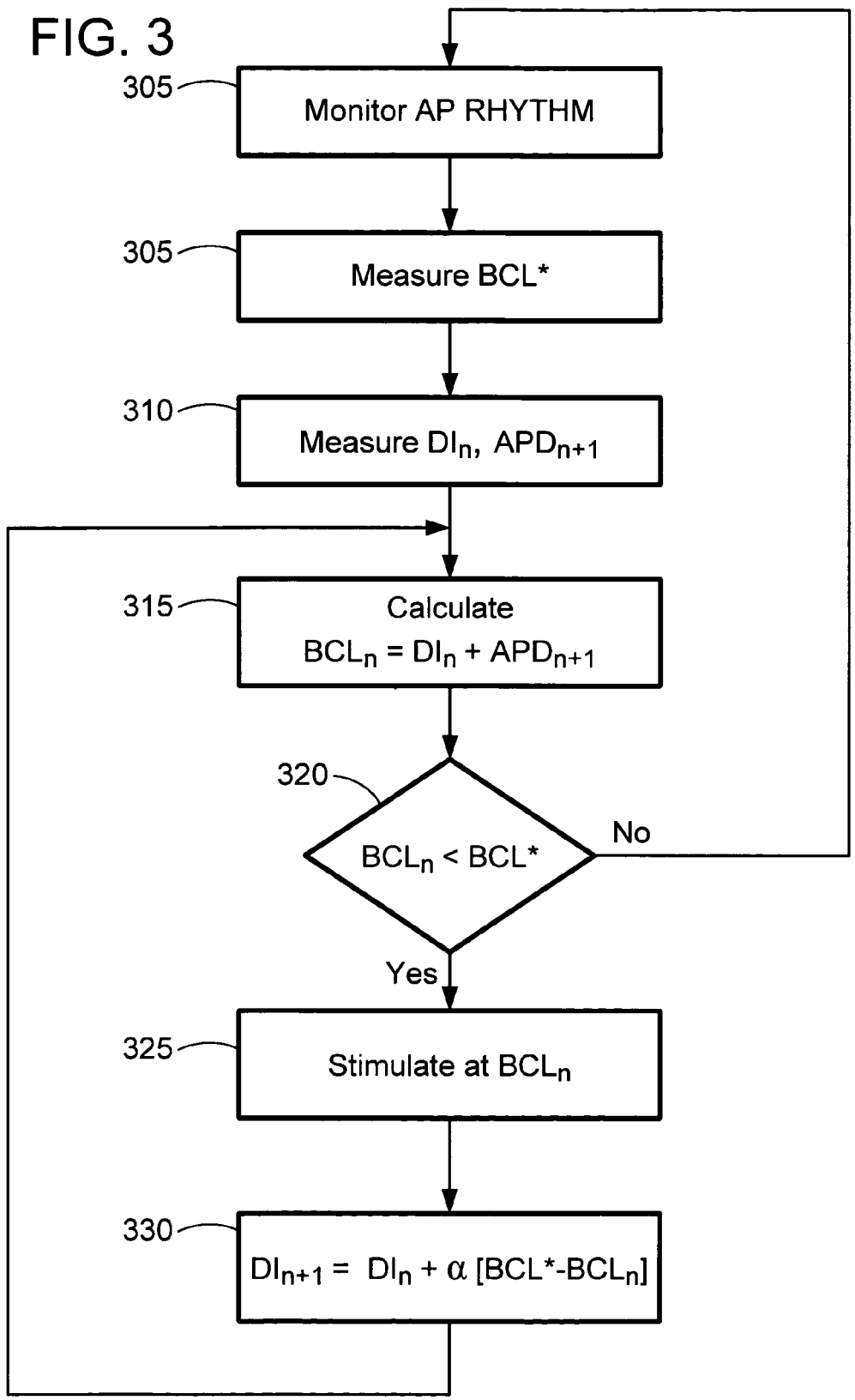

DFC

ADIC

Beat number (n)

ADAPTIVE DIASTOLIC INTERVAL CONTROL OF ACTION POTENTIAL DURATION ALTERNANS

CROSS-REFERENCE TO RELATED PATENT APPLICATIONS

This patent application claims the benefit of U.S. Provisional Patent Application No. 60/548,714, filed Feb. 27, 2004.

FIELD OF THE INVENTION

This invention pertains to a method and system that can be used to detect and eliminate unwanted dynamics in real-world, low-dimensional dynamical systems. More specifically, the present invention relates to a real-time detection technique and a real-time, adaptive, model-independent control technique for detecting and stabilizing pathological physiological rhythms, such as repolarization alternans, on the basis of the rate dependence of cardiac tissue.

BACKGROUND OF THE INVENTION

At slow heart rates in healthy hearts, the cardiac action potential (AP) in any given cell has a relatively constant duration on a beat-to-beat basis. Degeneration of this normal period-1 AP rhythm into higher-period or aperiodic rhythms may be closely linked to the initiation of spatiotemporal cardiac arrhythmias such as fibrillation.

Many of these cardiac arrhythmias can be characterized on the basis of the physical principles of nonlinear dynamics. Model-independent nonlinear dynamical control techniques therefore have been applied to periodic and aperiodic cardiac rhythms in an attempt to control these rhythm disturbances to restore the normal period-1 behavior.

Many of the model-independent control techniques that have previously been used to control cardiac dynamics stem from the Ott-Grebogi-Yorke (OGY) technique for controlling chaotic systems. OGY chaos control, however, requires sufficient observation of the chaotic system trajectory prior to the initiation of control so that the dynamics of the system can be learned. This allows the control algorithm to estimate the location and stability characteristics of the period-1 fixed point of the system. Control is then initiated by applying small perturbations to an accessible system parameter in an attempt to force the state of the system towards the period-1 fixed point. Applied to the heart, the most accessible system parameter available for perturbation is the timing of the next excitation, which can be advanced or (in some situations) delayed through low-magnitude current stimulation. The period between successive excitations is commonly referred to as the basic cycle length (BCL).

OGY-type control algorithms have been applied to rabbit ventricle preparations exhibiting pharmacologically induced, aperiodic (possibly chaotic) interbeat intervals. The aperiodic nature of the rhythm allowed the electrophysiological dynamics to be learned, because the system repeatedly visited the neighborhood of the target period-1 fixed point. The inter-beat intervals were successfully controlled to a period-3 rhythm, but the desired period-1 rhythm was not obtained. In another study of aperiodic dynamics, a cardiac-specific control algorithm applied to a simulated chaotic action potential duration (APD) time series was successful in controlling to the unstable period-1 rhythm at certain excitation rates.

The control algorithms used in both of the aforementioned studies require pre-control learning stages. Such learning stages may be clinically unacceptable because they could result in a dangerous delay in the termination of an arrhythmia. An additional problem with algorithms requiring a learning stage is that they are not generally applicable to stable periodic rhythms; For example, period-2 or higher-period rhythms typically do not visit the neighborhood of the unstable period-1 fixed point, and thus do not provide sufficient information for learning the stability characteristics of the period-1 fixed point. This problem is critical given that controlling periodic cardiac rhythms such as alternans (a period-2 alternation in the duration of a particular cardiac measurement) may be important, as experiments and computational models have demonstrated such rhythms to be causally linked to conduction block and the initiation of reentry.

Chaos control techniques that do not require a learning stage have thus been developed to control periodic systems. Delayed feedback control (DFC) algorithms have been used in a variety of modeling and experimental studies. These methods typically require (i) knowledge of the state of the system for a short time history, and (ii) a basic understanding of the system dynamics to ensure that the control perturbations are of the correct magnitude and polarity. These two elements allow the periodic rhythm to be stabilized by continuous adjustment of the accessible system parameter.

Both unrestricted DFC (which allow both lengthening and shortening of the BCL during control) and restricted DFC algorithms (which allow only shortening of the BCL) have been applied to cardiac rhythm disturbances. Unrestricted DFC has been used experimentally to control APD alternans in bullfrog heart preparations. Provided that the feedback proportionality constant in the algorithm was within an appropriate range of values, the period-2 alternans rhythm was successfully controlled to the underlying unstable period-1 rhythm. Unrestricted DFC has also been applied to control spatiotemporal APD alternans in simulated 1-dimensional Purkinje fibers.

Restricted DFC algorithms have been used to control atrio-ventricular (AV) node conduction alternans, a beat-to-beat alternation in the conduction time through the AV node, in rabbit heart preparations in vitro and human subjects in vivo. In both cases, AV node conduction alternans was successfully controlled to the underlying unstable period-1 fixed point. Restricting the control scheme to apply only unidirectional (shortening) perturbations to the excitation rate was found to increase the range of values of the feedback proportionality constant over which the period-1 fixed point could be stabilized.

When DFC algorithms are used to control periodic rhythms, rapid convergence to the period-1 rhythm is achievable only if the feedback proportionality constant is at or near an optimal value that is not known a priori. The optimal value of the feedback constant is a function of the degree of instability of the fixed point, making determination of the optimal value during periodic rhythms difficult. Algorithms containing a learning stage, during which external perturbations are applied to the system in order to explore the neighborhood of the period-1 fixed point, can be used to estimate this optimal value. Another limitation of existing DFC algorithms is that they fail if the proportionality constant lies outside an acceptable range of values that is not known a priori. While algorithms that iteratively adapt the feedback constant to achieve control do exist, such algorithms are sensitive to the noise and nonstationarities that are typically present in experiments.

Existing model-independent algorithms for the control of cardiac electrophysiological dynamics all share the OGY requirement of estimating some characteristics of the fixed-point dynamics. Although such algorithms have proved effective for controlling APD alternans, an alternative approach that requires no assumptions or estimations of the fixed-point dynamics is desirable.

The invention provides such an approach. These and other advantages of the invention, as well as additional inventive features, will be apparent from the description of the invention provided herein.

BRIEF SUMMARY OF THE INVENTION

In an exemplary embodiment, the present invention provides a control method that capitalizes on the rate dependence of excitable tissue such as cardiac tissue, neuronal tissue, and the like to control both periodic and aperiodic temporal rhythm disturbances to the underlying unstable period-1 rhythm. The control method of the present invention does not require the dynamics of the system to be learned, and it can be applied to control both noisy and drifting AP rhythms. Numerical simulations comparing the control method of the present invention with existing methods demonstrate that rapid convergence to the period-1 rhythm can be achieved over a wide range of parameter values with the present invention.

Unlike other control methods, which require a number of beats to locate the period-1 fixed point, the control method of the present invention locates the period-1 fixed point nearly instantaneously, rapidly eliminating any higher-period or aperiodic rhythms.

The present invention can also be applied to control realistic rhythm disturbances occurring at non-constant cycle lengths.

Other aspects, objectives and advantages of the invention will become more apparent from the following detailed description when taken in conjunction with the accompanying drawings.

BRIEF DESCRIPTION OF THE DRAWINGS

FIG. 3 is a flowchart illustrating an exemplary embodiment of an adaptive DI control method in accordance with the present invention;

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1A:
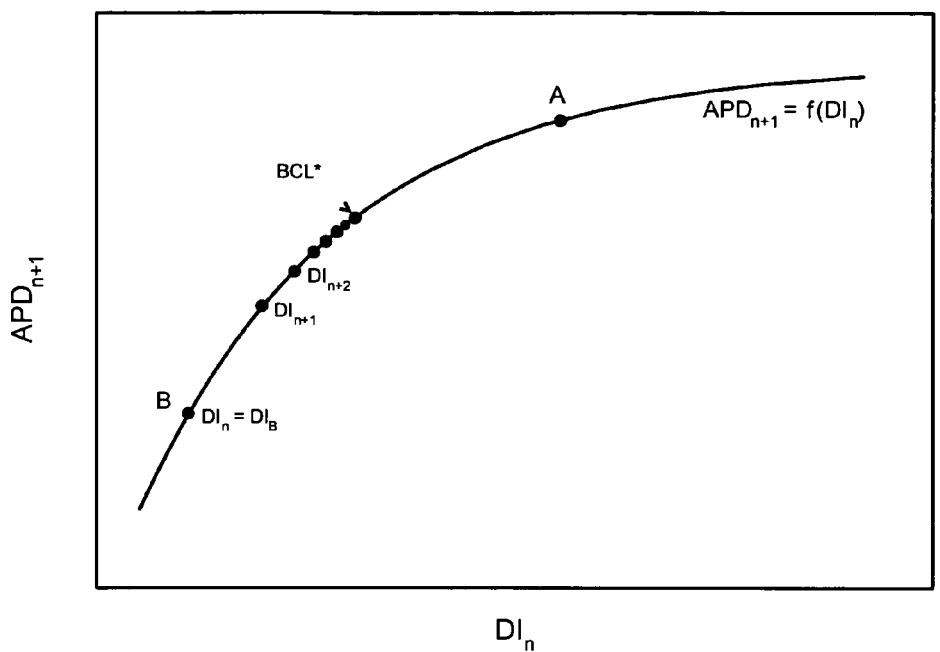
FIG. 1a illustrates the restitution relation between the $n^{th}$ diastolic interval ($DI_n$) and the $n+1^{th}$ action potential duration ($APD_{n+1}$) with the period-2 action potential (AP) rhythm occurring at a constant cycle length BCL* when diastolic interval (DI) and adaptive DI (ADI) control schemes in accordance with the present invention are applied to a stable period-2 AP rhythm.

The present invention provides a real-time detection technique and a real-time, adaptive, model-independent control technique for detecting and stabilizing pathological physiological rhythms, such as repolarization alternans, on the basis of the rate dependence of excitable tissue such as cardiac and neuronal tissue. In the description that follows, the invention shall be described using cardiac tissue. Those skilled in the art will recognize that the present invention may be used with other types of excitable tissue. The rate dependence of cardiac tissue is typically expressed through the restitution relation, the unique relationship existing between the $n^{th}$ diastolic interval ($DI_n$) and the $n+1^{th}$ action potential duration ($APD_{n+1}$), where n is the beat number. FIG. 1a shows an exemplary restitution curve. Expressed mathematically, this relationship is $APD_{n+1}=f(DI_n)$, where f is an experimentally determined function. While the control method of the present invention does not require f to be determined, it takes advantage of the unique relationship existing between $DI_n$ and $APD_{n+1}$.

Figure 1B:
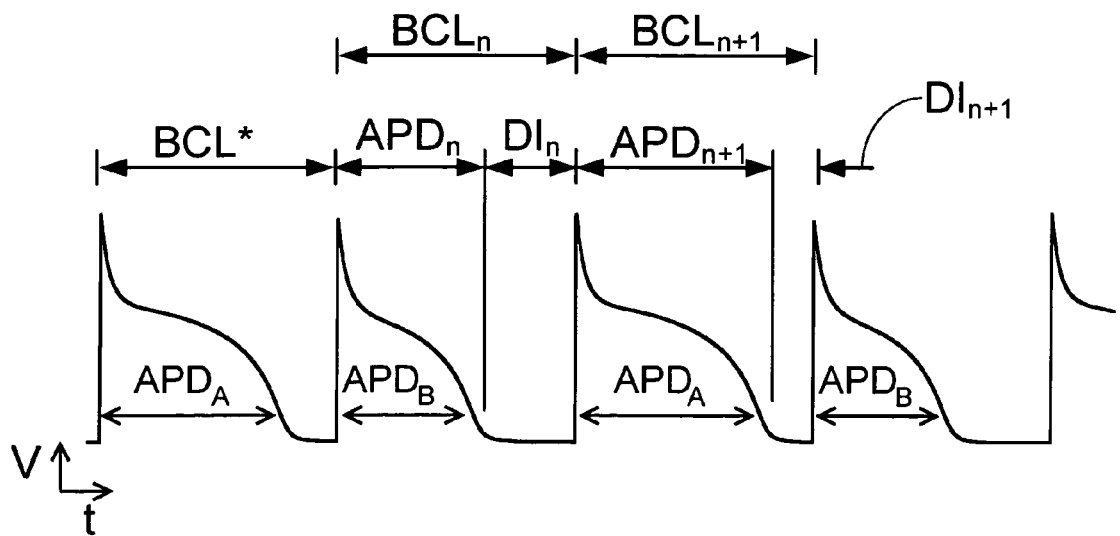
FIG. 1b illustrates the voltage profile of the alternans rhythm of FIG. 1a prior to the onset of control.

FIG. 1a illustrates the period-2 action potential (AP) rhythm occurring at a constant basic cycle length BCL* during pacing. FIG. 1b illustrates the voltage profile of this alternans rhythm prior to the onset of control. Prior to control, $APD_{n+1}$ alternates between points A and B of the restitution curve on a beat-to-beat basis. Because $APD_n + DI_n = BCL^*$, and $BCL^*$ is constant, $DI_n$ also alternates every beat. Using a process in accordance with the present invention referred to herein as diastolic interval (DI) control, the period-2 rhythm can be reduced to a period-1 rhythm by perturbing $BCL^*$ on a beat-to-beat basis so that $DI_n$ is kept at a constant target value. $BCL^*$ can be perturbed by advancing or delaying the timing of the next AP pulse using known stimulation techniques. For example, making the target DI equal to the DI at point B on the restitution curve of FIG. 1a results in $DI_n = DI_{n+1} = DI_B$ during DI control. Due to the functional dependence of $APD_{n+1}$ on $DI_n$ characterized by the restitution curve, pacing with identical consecutive diastolic intervals causes each subsequent APD to rapidly adjust to a constant repeating morphology. For example, DI control with a target DI equal to $DI_B$ results in $APD_{n+1} = APD_{n+2} = APD_B$. In other words, initiation of DI control when $DI_n = DI_B$ makes every subsequent DI equal to $DI_B$, and hence each subsequent APD will be equal to $APD_B$. The resulting period-1 AP rhythm (characterized by the sequence $DI_B$, $APD_B$, $DI_B$, $APD_B$ . . . ) occurs at a cycle length of $BCL_B = DI_B + APD_B$. Because of the uniqueness of the restitution curve at steady state, any one target DI will be followed by only one unique value of APD during DI control. Thus, the period-1 fixed point can be obtained for any BCL by adjusting the target DI value and obtaining the corresponding APD using DI control.

Figure 2:
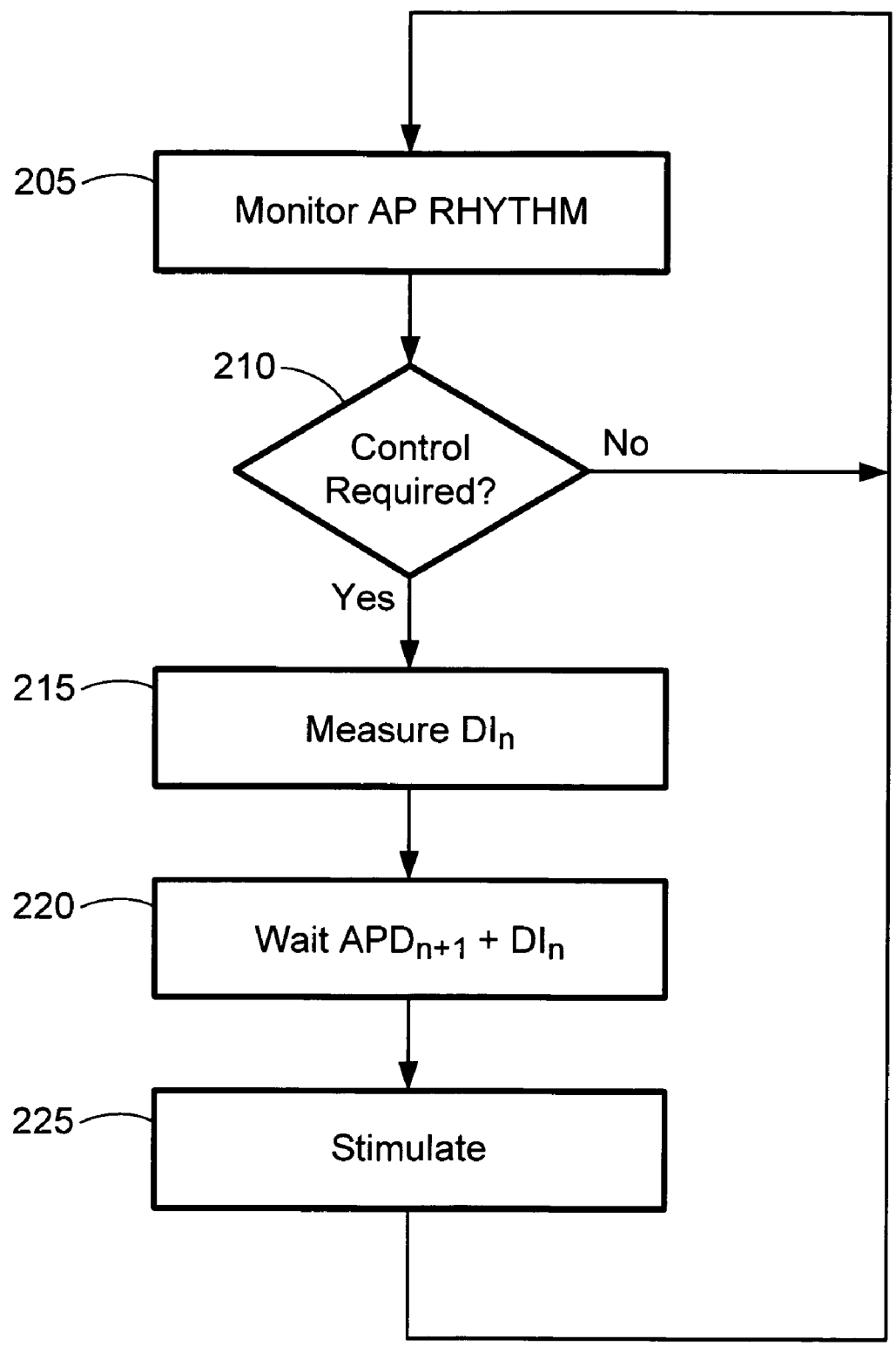
FIG. 2 is a flowchart illustrating an exemplary embodiment of a DI control method in accordance with the present invention.

FIG. 2 is a flowchart illustrating an exemplary embodiment of a DI control method in accordance with the present invention. Initially, the method monitors the AP rhythm (205) to determine if intervention is required (210). Such monitoring and the decision to apply control can be carried out in known ways, as appropriate. If intervention is required, operation proceeds to step 215 in which the current diastolic interval ($DI_n$) is measured. Any suitable technique to measure the DI can be used.

At step 220, the process waits until the end of the next AP pulse; i.e. until $APD_{n+1}$ has elapsed and then waits an additional interval equal to the diastolic interval of the previous pulse; i.e., $DI_n$. At step 225, stimulation is applied so as to induce another AP pulse. In this way, the DI following $APD_{n+1}$, namely $DI_{n+1}$ is controlled to be the same as the prior diastolic interval, $DI_n$. The process repeats by looping back to step 205.

Existing delayed feedback control (DFC) algorithms target the period-1 fixed point at the original cycle length by making progressively smaller perturbations to the cycle length. An adaptive DI (ADI) control technique in accordance with the present invention involves selecting an initial target DI and then adjusting this value on a beat-to-beat basis until the sum of the target DI and subsequent APD is equal to the original basic cycle length $BCL^*$ (i.e., $DI_n + APD_{n+1} = BCL^*$).

Given any non-period-1 APD rhythm occurring at a constant cycle length $BCL^*$, ADI control can be initiated at any time provided that $BCL_n < BCL^*$, where $BCL_n = DI_n + APD_{n+1}$. If this criterion is satisfied, DIn becomes the target DI. The first ADI control perturbation is thus applied a short time (of duration $DI_n$) after $APD_{n+1}$. After the first control perturbation is applied, each successive DI is adjusted according to the following control rule:

$$DI_{n+1} = DI_n + \alpha[BCL^* - BCL_n], \quad (1)$$

where $\alpha$ is a constant between 0 and 1 which controls the rate at which $DI_n$ changes. Provided that the starting criterion $BCL_n < BCL^*$ is met, this control rule adaptively lengthens the target DI on a beat-to-beat basis such that the difference between the present cycle length ($BCL_n$) and the original cycle length ($BCL^*$) is reduced. When $BCL_n = BCL^*$, the period-1 rhythm will have been restored at the original cycle length $BCL^*$.

FIG. 1a illustrates the methodology of ADI control when controlling a period-2 APD alternans rhythm to the underlying unstable period-1 fixed point. During pacing at the original cycle length ($BCL^*$), the action potentials oscillate between points A and B on the restitution curve during the period-2 rhythm. ADI control is initiated immediately after the short action potential occurs (i.e., point B on the restitution curve), because $DI_B + APD_B < BCL^*$. By increasing $DI_n$ during the subsequent beats in accordance with Equation 1 (equivalent to moving up the restitution curve to $DI_{n+1}$, $DI_{n+2}$ and beyond as shown in FIG. 1A), $BCL_n$ ($= DI_n + APD_{n+1}$) gradually increases until $BCL^*$ is reached. As FIG. 1a shows, this leads to the period-1 fixed point at $BCL^*$; i.e., when $BCL^*$ is reached, the period-1 rhythm at the original cycle length is restored.

Initiating ADI control when $BCL_n < BCL^*$ and then progressively lengthening the cycle length until the original cycle length is reached assumes that it is not possible to excite the system at a rate slower than some intrinsic systemic rate. Such unidirectional perturbations constitute a restricted form of ADI control. However, if bi-directional perturbations to the cycle length are possible, unrestricted ADI control may be initiated at any time, as both shortening and lengthening of the cycle length are allowed with the same control method.

FIG. 3 is a flowchart of an exemplary embodiment of an adaptive DI control method in accordance with the present invention. Initially, the method monitors the AP rhythm (305) and determines the original cycle length $BCL^*$ (310). The DI interval of the current cycle ($DI_n$) and the subsequent APD ($APD_{n+1}$) are then measured (315) and summed (320) to calculate $BCL_n$. If $BCL_n$ is not less than $BCL^*$, as determined at 325, operation loops back to the monitoring step (305). If, however, $BCL_n$ as calculated in step 320 is less than $BCL^*$, operation proceeds to step 330 in which a perturbation is applied at the time $BCL_n$ ($= APD_{n+1} + DI_n$) after the start of the last AP pulse. The next diastolic interval, $DI_{n+1}$, is then calculated at step 335 in accordance with equation 1, and the method loops back to 320 and continues as described.

An exemplary embodiment of an ADI control method in accordance with the present invention has been compared to a restricted delayed feedback control (DFC) method applicable to cardiac AP rhythm disturbances. The restricted DFC method involves perturbing the BCL on a beat-to-beat basis according to the following rule:

$$\overline{BCL_n} = \begin{cases} BCL^* + \Delta BCL_n & \text{if } \Delta BCL_n < 0, \\ BCL^* & \text{if } \Delta BCL_n \geq 0, \end{cases} \quad (2)$$

where $$\Delta BCL_n = \lambda(APD_n - APD_{n-1}), \quad (3)$$

and $$\overline{BCL_n} = APD_n + DI_n. \quad (4)$$

In the above equations, BCL* is the pacing period without control and λ is the constant feedback gain.

In comparing the method of the present invention to the above DFC method, single-cell simulations were performed using the Fox-McHarg-Gilmour canine ventricular myocyte (CVM) model and two one-dimensional map models using custom programs written in C. All simulations conducted with the CVM model were repeated using the Luo-Rudy 1 (LR1) ionic model. For brevity, not all results from the LR1 simulations are shown. Unless otherwise noted, LR1 results were qualitatively similar to those obtained with the CVM model. For the CVM and LR1 models, forward Euler numerical integration schemes were used for all simulations, with time steps of 0.0025 ms for the CVM model and 0.01 ms for the LR1 model. We set $g_{Na}$=16.0 μS/cm2, $g_{si}$=0.06 μS/cm2, and $g_K$=0.432 μS/cm2 in the LR 1 model.

The restitution curve of the 1-dimensional Hall-Gauthier (HG) map model is $$APD_{n+1} = 392.0 - 525.3 \exp(-DI_n/40.0). \quad (5)$$

The restitution curve of the 1-dimensional Watanabe-Gilmour (WG) map model is $$APD_{n+1} = \begin{cases} 3.1 \times 10^{-10} DI_n^8 - 4.9 \times 10^{-8} DI_n^7 + 2.4 \times 10^{-6} DI_n^6 \\ -3.4 \times 10^{-5} DI_n^5 - 3.1 \times 10^{-4} DI_n^4 + 1.4 \times 10^{-2} DI_n^3 \\ -19 DI_n^2 + 0.93 DI_n + 1.39.2, DI_n < 15 \text{ ms}, \\ 2.7 \times 10^{-3} DI_n^2 - 20 DI_n + 137.5, DI_n \geq 15 \text{ ms}. \end{cases} \quad (6)$$

Drift was introduced to the HG map model by shifting the restitution curve slightly after each beat. The drifting map model was $$APD_{n+1} = 392.0 - 525.3 \exp[-DI_n/(40.0+\phi_n)], \quad (7)$$

where $\phi_{n+1} = \phi_n + 0.35$ and $\phi_0 = 0$.

Noise can be added to the HG map model by adding a random term to the restitution curve. A drifting, noisy version of the HG restitution curve is $$APD_{n+1} = 392.0 - 525.3 \exp[-DI_n/(40.0+\phi_n)] + \zeta_n, \quad (8)$$

where $\phi_{n+1} = \phi_n + 0.35$ and $\phi_0 = 0$. In Equation 8, $\zeta_n$ is a normally distributed variable with a mean of zero and a constant standard deviation.

To simulate a sequence of randomly fluctuating cycle lengths in the CVM model, a normally distributed random term with a mean of zero and a constant standard deviation can be added to the diastolic interval between each beat.

The utility of the ADI control algorithm for eliminating rhythm disturbances in spatially extended cardiac tissue was tested by applying it to control a period-2 APD alternans rhythm occurring in a 1-dimensional Purkinje fiber. The fiber model was identical to that used by Echebarria and Karma, who performed similar simulations using an unrestricted DFC algorithm.

Briefly, the fiber model can be defined by the 1-dimensional cable equation $$\frac{\partial V}{\partial t} = D \frac{\partial^2 V}{\partial x^2} - \frac{I_{ion} + I_{stim}}{C_m}, \quad (9)$$

where V is the membrane potential, D is the diffusion constant of the tissue, $I_{ion}$ is the sum of the transmembrane ionic currents, $I_{stim}$ is the externally applied stimulus current, and $C_m$ is the membrane capacitance. To be consistent with Echebarria and Karma, the Noble Purkinje fiber model with D=0.00025 cm²/ms, and $C_m$=12 μF/cm² was used. The cable length was varied between 0.5 cm and 5 cm in steps of 0.5 cm. Each length of cable was paced at cycle lengths between 270 ms and 150 ms, starting at 270 ms and then stepping down in increments of 5 ms after 200 stimuli at each BCL. APD was calculated at a threshold of −40 mV. All simulations were carried out using a forward Euler integration scheme, with a temporal step size of 0.05 ms and a spatial step size of 0.01 cm.

Figure 4A:
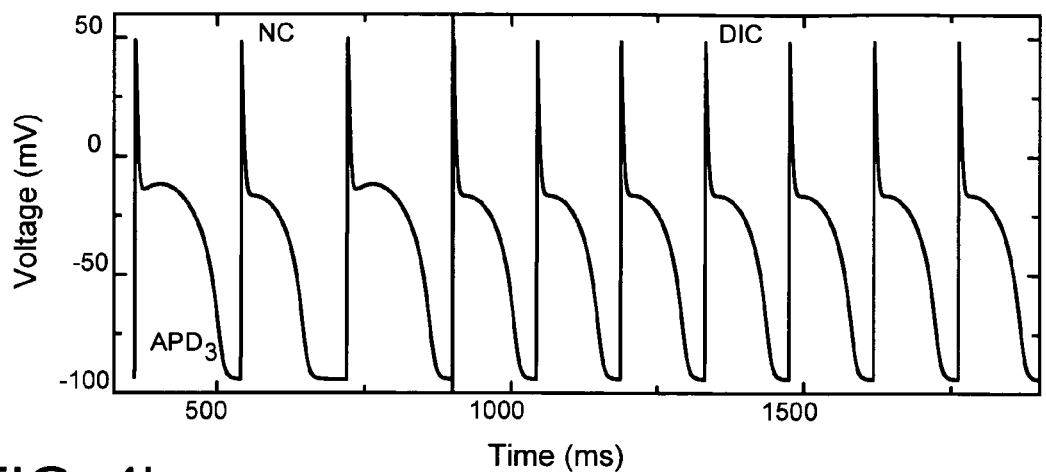
FIGS. 4a-4c illustrate the DI control of the present invention applied to the Fox-McHarg-Gilmour canine ventricular myocyte (CVM) model of the ventricular action potential.
Figure 4B:
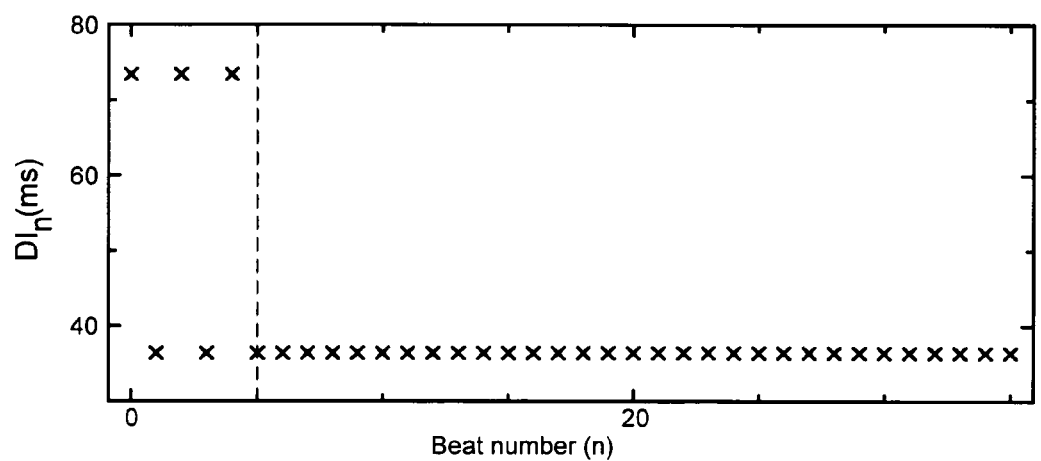
Figure 4C:
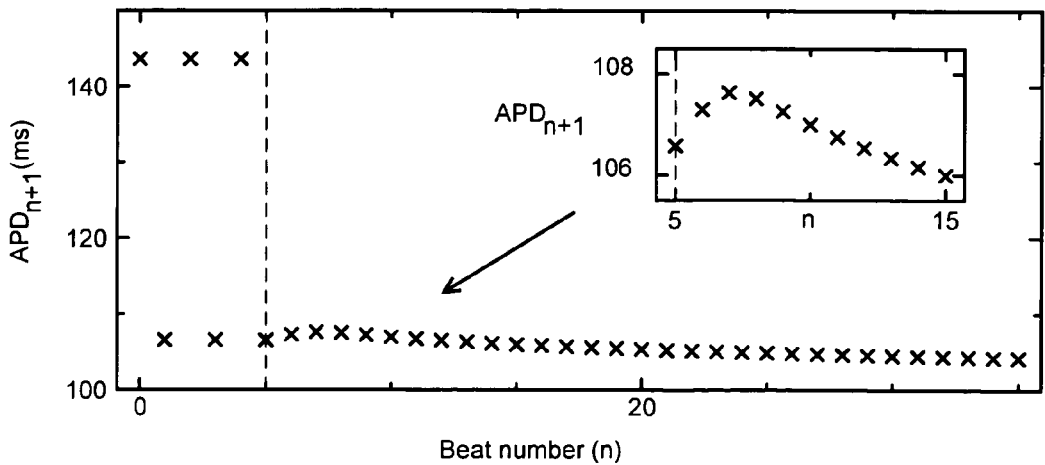

Now that the principles of the invention have been described, experimental results shall now be discussed. FIGS. 4A-4C illustrate the application of the DI control method of the present invention to the Fox-McHarg-Gilmour canine ventricular myocyte (CVM) model of the cardiac action potential. Control was initiated after the sixth beat so that the target DI was equal to the DI preceding the short APD during alternans. FIGS. 4A-4C show that after an initial period during which the AP adjusts to the new DI, the AP quickly settles down to a regular morphology of constant duration at the control DI.

As shown in FIG. 4a, after 6 beats of an APD alternans rhythm at a cycle length of 180 ms with no control (NC), the target DI is set equal to the DI preceding the short action potential during alternans, and DI control (DIC) is initiated (n≧6 onwards, dotted line). During control, every DI is set equal to the target DI, as shown in FIG. 4b. As shown in FIG. 4c, the action potential quickly settles into a steady period-1 rhythm where every action potential has identical duration. Note that the first APD shown in FIG. 4c corresponds to $APD_1$ while the first DI shown in FIG. 4b corresponds to $DI_0$, the DI preceding the first action potential ($APD_1$).

The rate at which the AP adjusts to a constant morphology after initiation of DI control is dependent upon memory. Memory is the slowly accumulating and dissipating influence of BCL on APD and has a time course on the order of seconds or minutes. If the AP is strongly dependent upon the stimulation history, the AP may take a number of beats to adjust to a constant repeating morphology during DI control. However, if little or no memory is present, the AP will adjust almost instantaneously to a unique value corresponding to the target DI.

As FIGS. 4a-4c illustrate, the CVM model takes a number of beats to adjust to a steady-state AP morphology, indicating that memory of the previous BCL is relatively strong and dissipates slowly. However, the same simulation conducted with the LR1 model shows the AP adjusting much more quickly to a steady-state morphology, indicating that memory of the previous BCL is relatively weak and dissipates rapidly in the LR1 model (data not shown). It should also be noted that even though the DIs preceding the second ($APD_2$), fourth, and sixth APs in FIGS. 4a-4c are identical to the DIs preceding the seventh and subsequent APs, the durations of the second, fourth, and sixth APs are different from the APD at steady state (i.e., after the transient period) during DI control. This difference in APD may be attributed to the contribution of memory to APD in the presence or absence of APD alternans. In the CVM model, the presence of APD alternans makes the short AP longer than if alternans was not present.

Figure 5A:
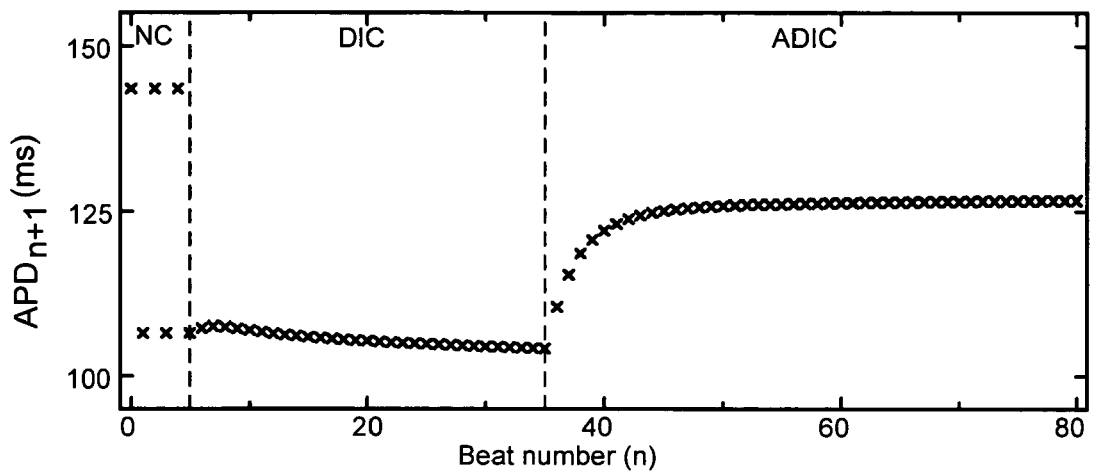
FIGS. 5a-5c illustrate the application of ADI control (ADIC) after DI control (DIC), in accordance with the present invention.
Figure 5B:
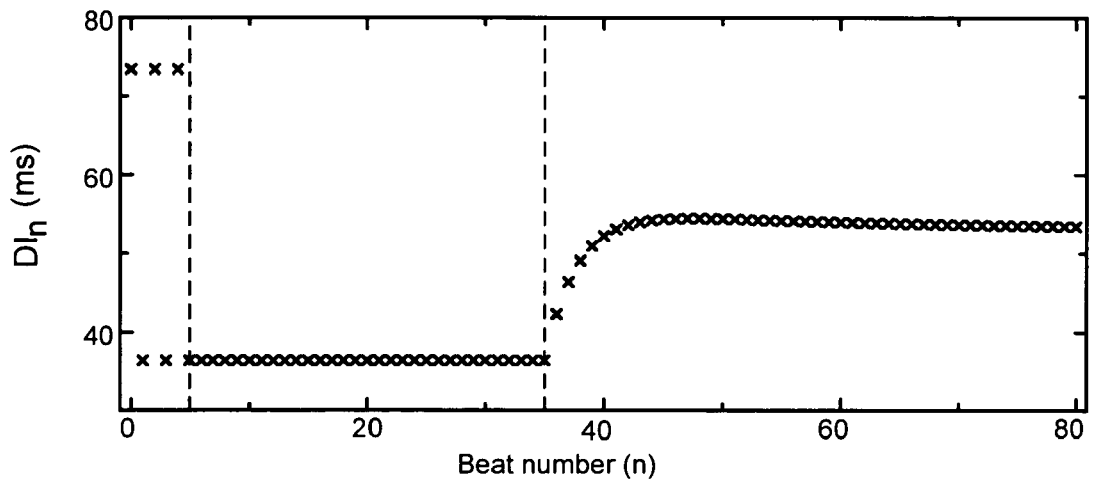
Figure 5C:
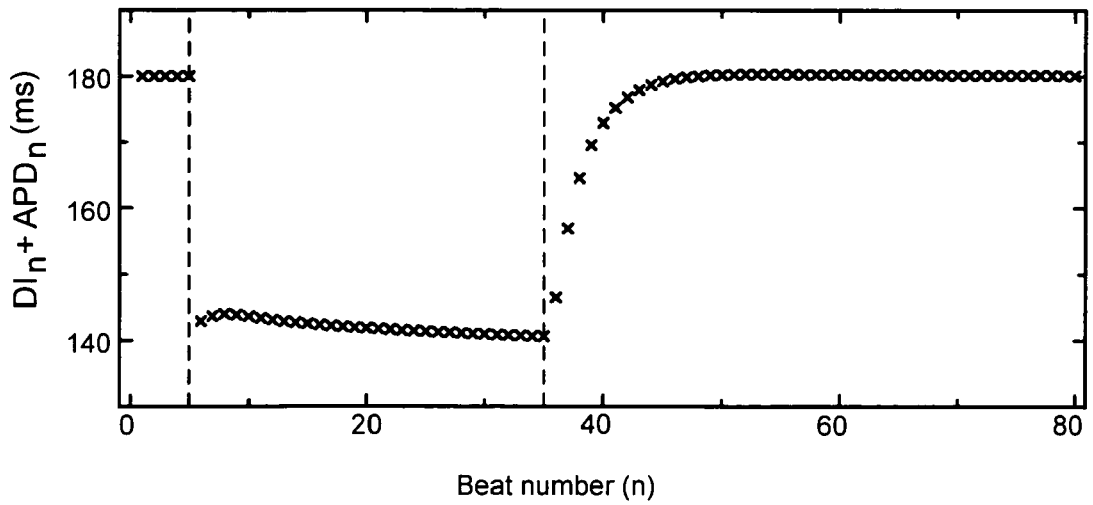

Taking the same period-2 rhythm illustrated in FIGS. 4A-4C and applying ADI control after DI control in accordance with the present invention results in the APD and DI sequences shown in FIGS. 5A-5C. Following an iterative adjustment in the target DI value, ADI control successfully locates the period-1 fixed point at the original BCL (BCL*).

In FIGS. 5A-5C, the data prior to the initiation of ADI control is identical to that in the case illustrated in FIGS. 4A-4C. The original cycle length (BCL*) was 180 ms before DI control was initiated. After a brief period of DI control, the ADI control method quickly adjusted the target DI according to Equation 1 such that the cycle length was again equal to BCL*, thus obtaining the period-1 fixed-point rhythm at the original excitation rate. In FIG. 5a, the first data point corresponds to $APD_1$, while in FIG. 5b, the first data point corresponds to $DI_0$ (the DI preceding $APD_1$). The first data point in FIG. 5c corresponds to $APD_1+DI_1$. During ADI control, $\alpha=0.15$.

Figure 6A:
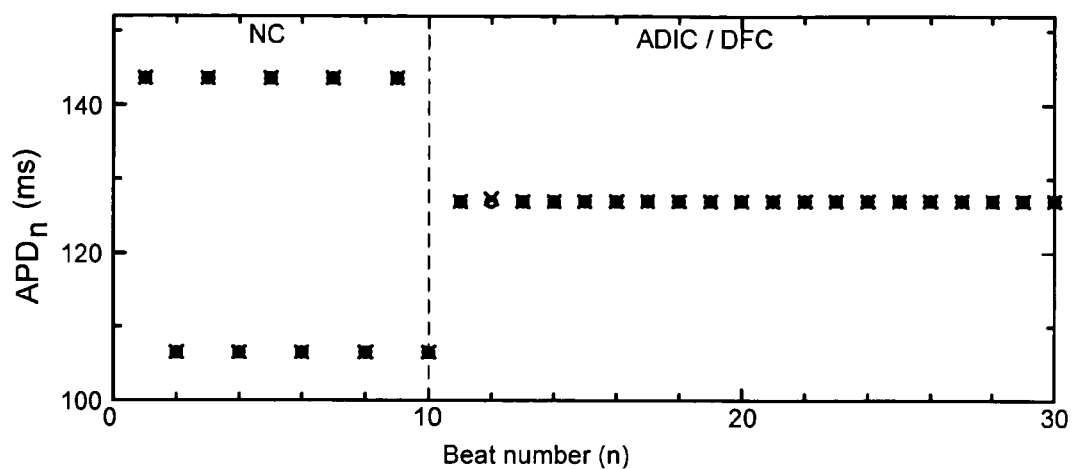
FIGS. 6a and 6b shows the convergence pattern of an ADI control (ADIC) method in accordance with the present invention and the convergence pattern of a delayed feedback control (DFC) method applied to a period-2 APD alternans rhythm.
Figure 6B:
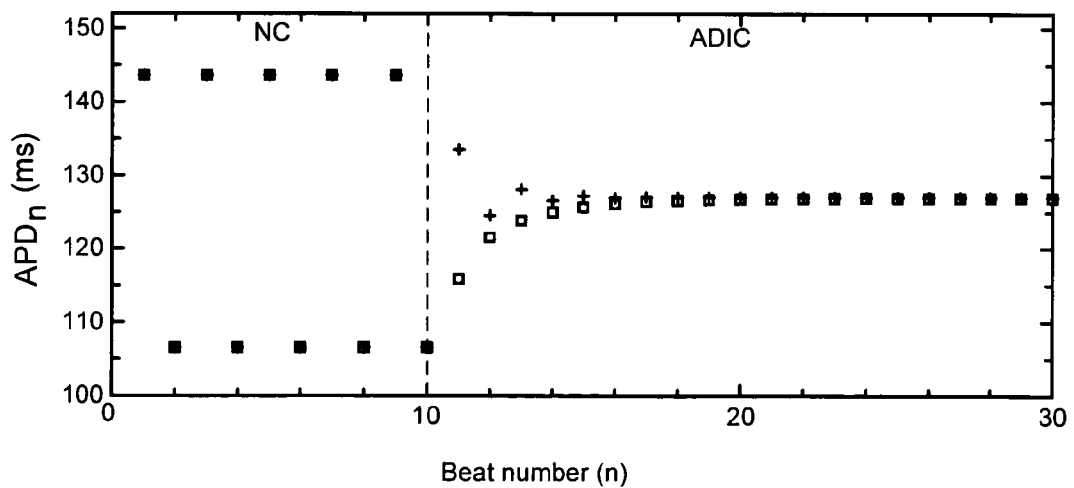

The convergence rates for the ADI and DFC algorithms are governed by the values of the proportionality constants $\alpha$ and $\lambda$, respectively. FIGS. 6a and 6b compare the typical convergence characteristics of the ADI control and restricted DFC algorithms applied to a period-2 APD alternans rhythm in the CVM model. In this comparison, $\alpha$ and $\lambda$ have been optimized a priori by scanning all possible values to obtain the most rapid convergence possible. The model was initially stimulated at a cycle length of 180 ms. FIG. 6a compares the two algorithms with $\alpha=0.47$ (ADIC, crosses) and $\lambda=0.53$ (DFC, circles). These feedback parameter values produced the most rapid convergence at a cycle length of 180 ms for each algorithm (within the parameter ranges $0 \leq \alpha \leq 1$ and $0 \leq \lambda \leq 1$). As FIG. 6a shows, both algorithms locate the period-1 fixed point almost instantaneously after control is initiated. FIG. 6b illustrates how the convergence characteristics of the ADI control algorithm are influenced by the value of $\alpha$ selected for the CVM model. Simulations are shown for $\alpha=0.2$ (squares; asymptotic convergence to fixed point) and $\alpha=0.65$ (pluses; oscillatory convergence to fixed point), NC=no control.

FIGS. 7a-7f compare the domains of control for the restricted DFC and ADI control algorithms of the present invention during alternans in the HG, LR1, and CVM models. As FIGS. 7a-7f show, the ADI control of the present invention succeeds over a comparable range of proportionality constant values for the LR1 and CVM models as the restricted DFC algorithm and succeeds over a much wider range of values for the HG map model.

Figure 7A:
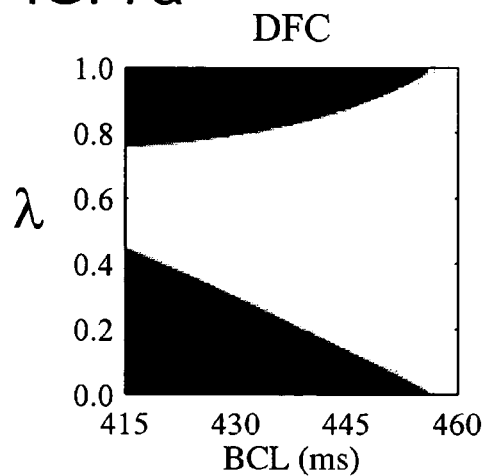
FIGS. 7a-7b show the domains and rates of convergence of an ADI control (ADIC) method in accordance with the present invention and a DFC method, as applied to the Hall-Gauthier (HG) map model.
Figure 7B:
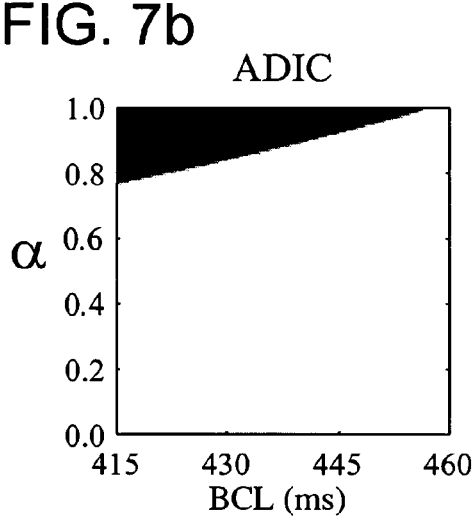
Figure 7C:
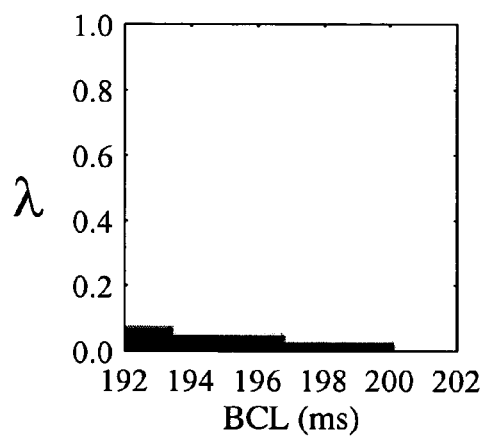
FIGS. 7c-7d show the domains and rates of convergence of an ADI control (ADIC) method in accordance with the present invention and a DFC method, as applied to the Luo-Rudy 1 (LR1) map model.
Figure 7D:
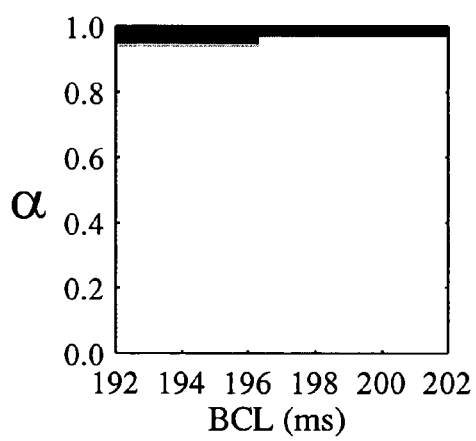
Figure 7E:
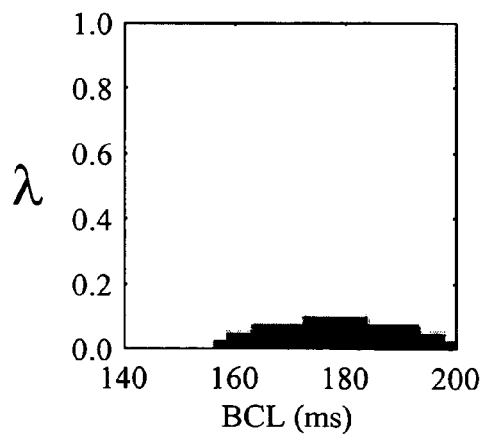
FIGS. 7e-7f show the domains and rates of convergence of an ADI control (ADIC) method in accordance with the present invention and a DFC method, as applied to the CVM model.
Figure 7F:
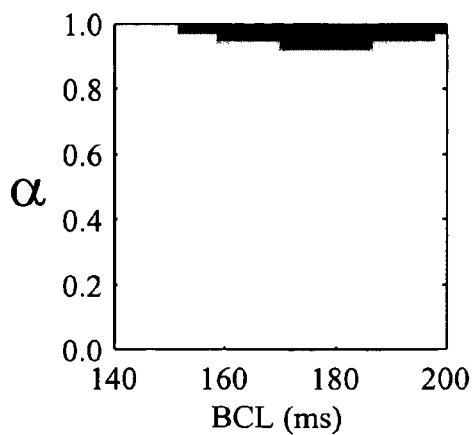

FIGS. 7a-7b compare the domains of control of the delayed feedback control (DFC) and adaptive diastolic interval control (ADIC) algorithms of the present invention applied to the HG map model. FIGS. 7c-7d compare the domains of control of the delayed feedback control (DFC) and adaptive diastolic interval control (ADIC) algorithms of the present invention applied to the Luo-Rudy 1 model. FIGS. 7e-7f compare the domains of control of the delayed feedback control (DFC) and adaptive diastolic interval control (ADIC) algorithms of the present invention applied to the Fox-McHarg-Gilmour canine ventricular myocyte models. All simulations were run for 600 beats, and convergence to the period-1 fixed point was judged to have occurred if $|APD_n - APD_{n-1}| < 0.5$ ms in each model. White regions in the figures indicate combinations of feedback parameter value ($\alpha$ or $\lambda$) and basic cycle length (BCL) where control successfully established a period-1 rhythm. Black regions in the figures indicate control failure. FIGS. 7a and 7b show that ADI control successfully converges to the period-1 fixed point over a wider range of proportionality constant values than DFC for the HG map model. FIGS. 7b and 7c and FIGS. 7e and 7f indicate that ADI control successfully converges to the period-1 fixed point over a comparable range of proportionality constant values to DFC for the LR1 and CVM models.

Figure 8A:
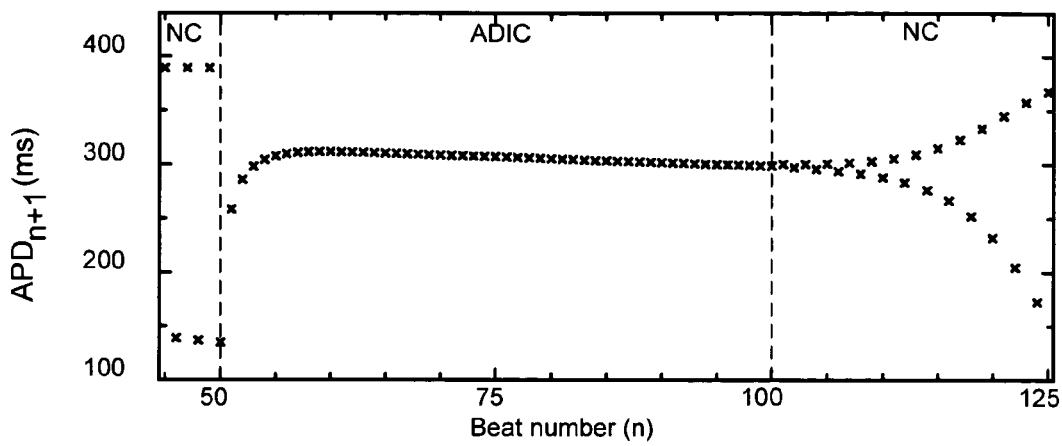
FIGS. 8a and 8b illustrate the application of ADI control in accordance with the present invention to a drifting version of the HG map model.
Figure 8B:
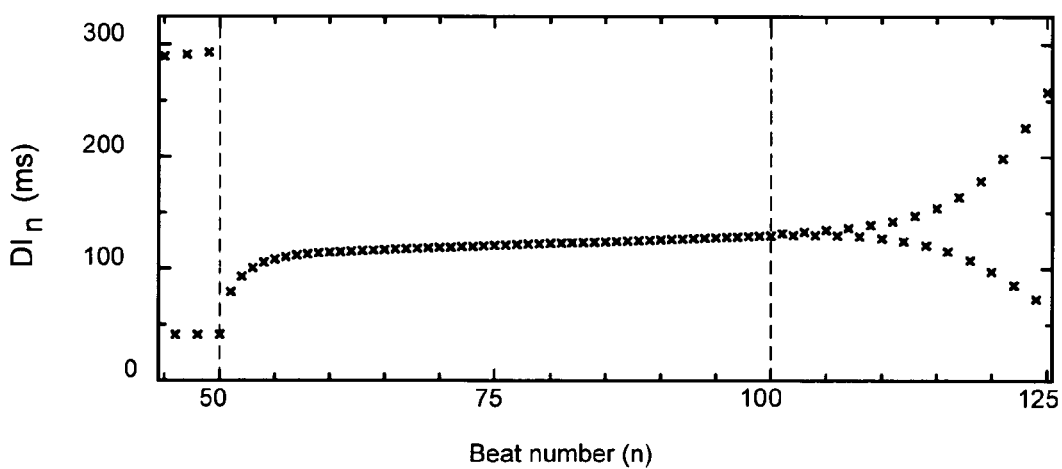

FIGS. 8A and 8B illustrate that the ADI control method of the present invention is able to track a drifting period-1 fixed point. In this simulation, ADI control was applied during beats 50 to 100 and drift was introduced into the HG map model by incrementally shifting the restitution curve on a beat-to-beat basis according to Equation 7. Also, $\alpha=0.15$, and BCL=430 ms. As shown, the unstable period-1 fixed point shifts to longer and longer diastolic intervals (FIG. 8b), and correspondingly shorter and shorter action potential durations (FIG. 8a), on a beat-to-beat basis, yet the ADI control method of the present invention easily tracks the fixed point. When control is removed after 100 beats (NC), the system reverts to a period-2 rhythm, illustrating that control success was not simply due to the disappearance of the period-2 fixed point as the restitution curve was drifting (i.e., drifting out of the period-2 regime).

Figure 9:
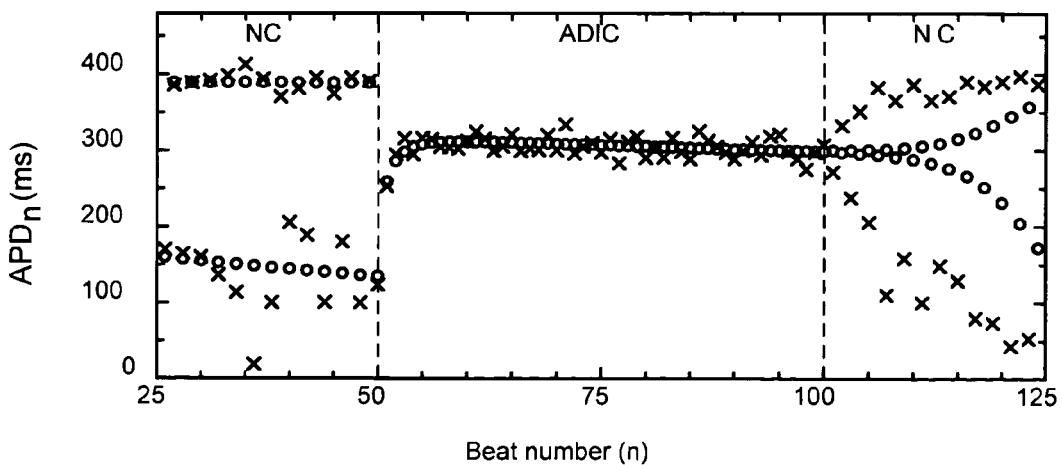
FIG. 9 illustrates the application of ADI control in accordance with the present invention to a drifting and noisy version of the HG map model.

ADI control in accordance with the present invention also successfully tracks a drifting period-1 fixed point in the presence of normally distributed, randomly varying noise. FIG. 9 compares the results of ADI control applied to a noisy APD signal with a drifting period-1 fixed point, to ADI control applied to an APD signal with identical drift but no noise.

In the simulations illustrated in FIG. 9, $\alpha=0.15$, BCL=430 ms, and the standard deviation of the noise is 10 ms. ADI control was applied during beats 50 to 100. The noisy data is shown as x's, while a map model exhibiting identical drift but no noise is shown as circles. ADI control succeeds in controlling the period-2 rhythm very close to the period-1 fixed point, despite the presence of noise. When control is turned off (NC), the presence of noise makes the action potential bifurcate to the period-2 rhythm much more quickly than in the model without noise.

Figure 10A:
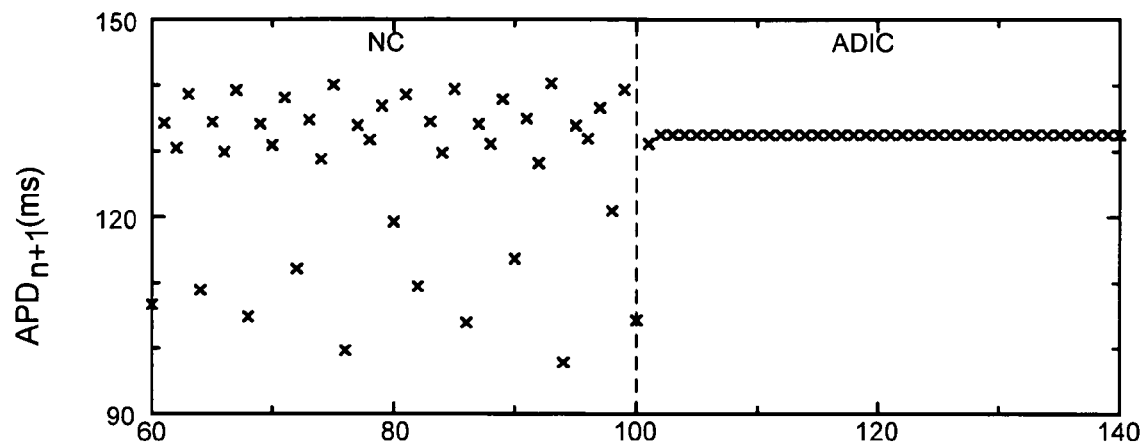
FIGS. 10a and 10b illustrate the application of ADI control in accordance with the present invention to the chaotic Watanabe-Gilmour (WG) map model.
Figure 10B:
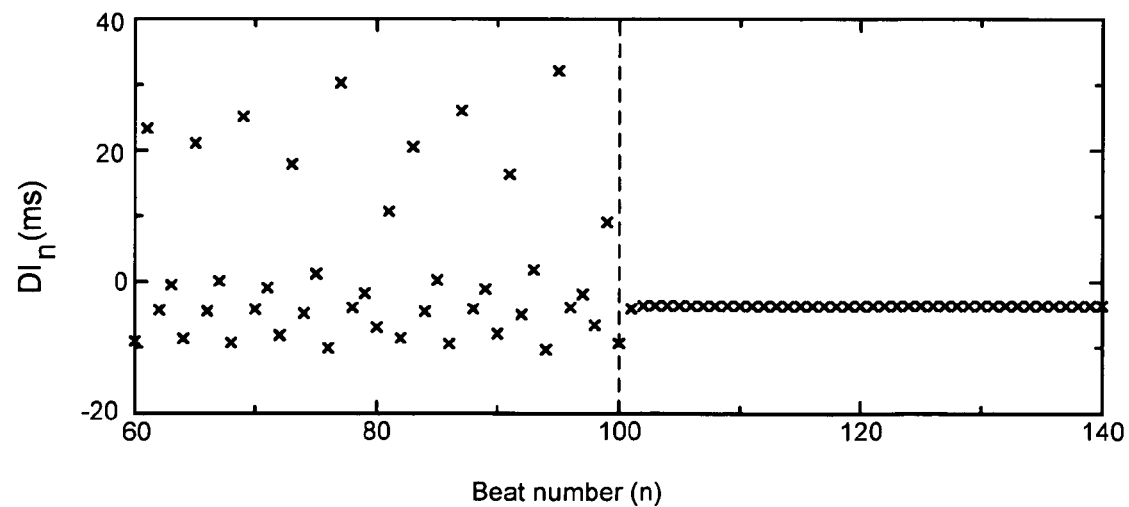

Even in the presence of large-amplitude noise, the control method of the present invention tracks the drifting period-1 fixed point effectively. Notably, ADI control also successfully converges to the underlying unstable period-1 fixed point of a constant-BCL chaotic APD time series, as shown in FIGS. 10a and 10b. In the simulation of FIGS. 10a and 10b, ADI control in accordance with the present invention was applied after beat 100 to the chaotic WG map model with $\alpha=0.15$, and BCL=130 ms. As illustrated by FIGS. 10a and 10b, ADI control successfully locates the period-1 fixed point of the original cycle length, even though this occurs at a negative diastolic interval.

Figure 11A:
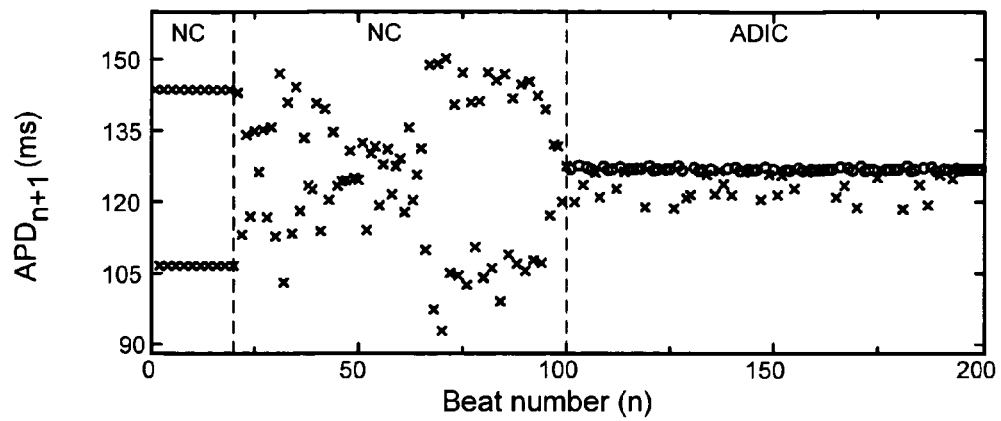
FIGS. 11a and 11b illustrate the application of ADI control in accordance with the present invention to a non-constant-BCL train of action potentials in the CVM model.
Figure 11B:
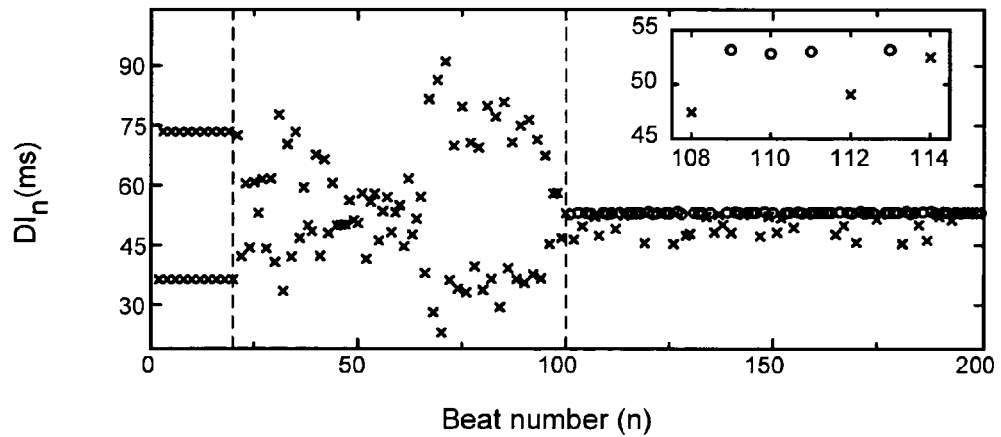

Existing control algorithms have focused on controlling action potential rhythms occurring at a constant BCL to the underlying period-1 fixed point of that BCL. Given that the excitation rate is unlikely to be constant during a real arrhythmia (i.e., in vivo), it is desirable to control an aperiodic non-constant-BCL AP activity in the CVM model with the ADI control of the present invention to establish a period-1 rhythm at a specific target BCL. Beats 21 to 100 in FIGS. 11a and 11b illustrate a non-constant-BCL AP rhythm with a mean cycle length of 180 ms, where fluctuations in the cycle length were created by randomly varying each diastolic interval. The standard deviation of the random fluctuation in the diastolic interval is 5 ms (n>21). For illustrative purposes, beats 1 to 20 demonstrate the presence of period-2 alternans at a constant cycle length of 180 ms. ADI control was initiated at beat number 101, with a target BCL of 180 ms. During control, if the random DI was shorter than the DI calculated by the ADI control algorithm (Equation 1), such a "spontaneous" beat elicited an AP (shown as the intermittent crosses from beat number 101 onwards). Random DI values that were longer than the DI values calculated by Equation 1, however, did not elicit APs, as the tissue was refractory to such spontaneous activity. As FIG. 11*a* shows, the fluctuation in BCL adds significant complexity to the AP rhythm ($21 \leq n \leq 100$). ADI control was implemented at beat number 101 so that the target BCL was 180 ms, with $\alpha=0.5$. Despite the fluctuations in cycle length, the period-1 fixed point of the target BCL is easily obtained using ADI control, thus illustrating the utility of the method of the present invention for controlling complex APD rhythms. As FIG. 11*a* shows, the ADI control algorithm is able to establish an approximately period-1 rhythm at the target BCL in the CVM model, with minimal disturbance from the spontaneous premature beats.

Given that the control algorithm cannot affect the premature spontaneous beats (shown as crosses in FIG. 11*b*), one might expect (due to the restitution effect of short DIs producing short APDs) that there would be little or no change in the pattern of short APDs when control is initiated. However, FIG. 11*a* shows that, in fact, the shortest APDs are eliminated. This dynamic results from the controlled shortening of the long APDs. By shortening a long APD, the next DI is lengthened (even if it is a spontaneous premature beat), thereby lengthening the next APD.

Figure 12:
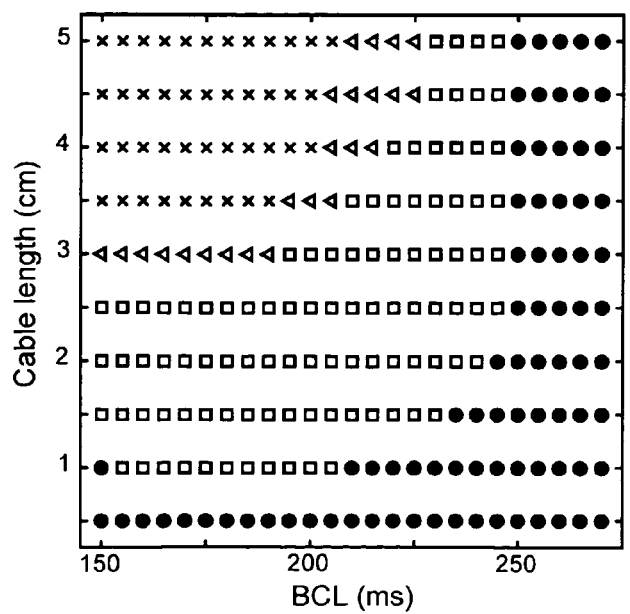
FIG. 12 shows the regions of different alternans behavior when ADI control in accordance with the present invention is applied to one end of a model 1-dimensional Purkinje fiber.

To be useful clinically, arrhythmia control algorithms must work not only in isolated cells but also in the spatially extended heart. The ability to eliminate alternans in the heart is potentially of great importance, given the evidence linking alternans, conduction block, and initiation of reentry. To investigate spatial control of APD alternans, the ADI control method of the present invention has also been applied to one end of a spatially extended 1-dimensional Purkinje fiber cable model exhibiting a period-2 APD alternans rhythm. FIG. 12 illustrates how the effectiveness of control of the invention in suppressing APD alternans changes as both excitation rate and cable length are varied. Specifically, ADI control of the present invention suppresses alternans along the entire length of the cable for large values of BCL, but the ability to suppress alternans along the entire length of the cable diminishes as the excitation rate increases.

In the simulations of FIG. 12, the fiber length was varied between 0.5 cm and 5 cm, and the BCL was varied between 150 ms and 270 ms. The Noble model of the Purkinje fiber was used, and $\alpha=0.1$. The symbols used in FIG. 12 correspond to no alternans (stars), first harmonic standing waves (squares), traveling discordant alternans (triangles), and conduction block (x's). Apart from a few minor differences occurring predominantly at the transitions between different alternans behaviors, the results illustrated in FIG. 12 are similar to those obtained for unrestricted DFC applied to control spatiotemporal APD alternans in simulated 1-dimensional Purkinje fibers.

These results suggest that the ability to suppress alternans or higher-order rhythms in a spatially extended system when controlling from one site is independent of the control method used. However, both the DFC and ADI methods use information about the system from the control site only to make decisions about when to apply the next stimulus. Thus, improved control may be possible by utilizing information about the dynamics occurring far from the control site.

Figure 13:
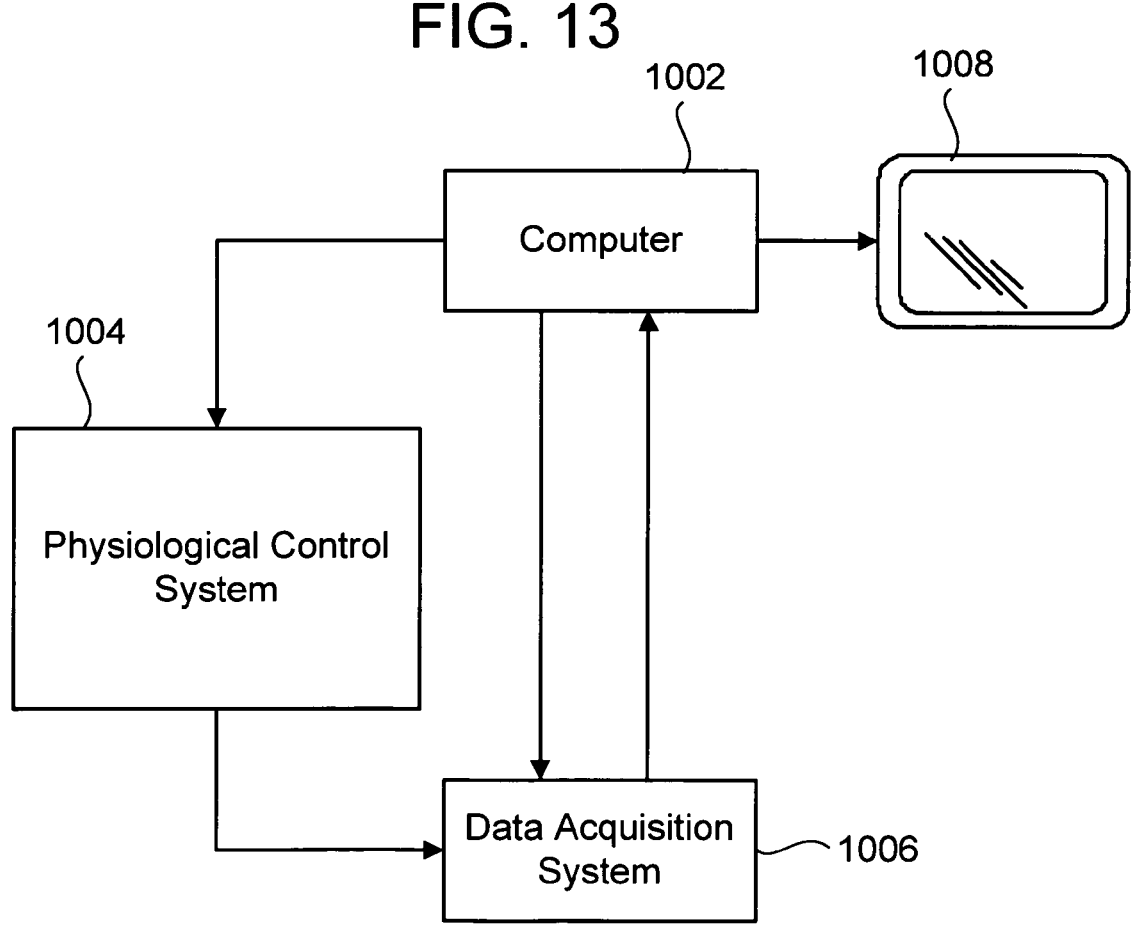
FIG. 13 is a block diagram generally illustrating an exemplary computer system on which the present invention may operate.

A block diagram of an exemplary system 1000 for implementing the invention is shown in FIG. 13. The exemplary system includes a computer 1002, a physiological control system 1004, a data acquisition system 1006, and display 1008. The physiological control system 1004, data acquisition system 1006 and display 1008 are well known in the art and need not be described in detail herein. In general terms, the computer 1002 controls the electrical stimulation of excitable tissue (e.g., cardiac tissue, neuronal tissue, etc.) in the physiological control system 1004. The physiological control system 1004 performs the stimulation of the tissue and obtains the action potential rhythms. The computer 1002 also controls the data acquisition system 1006, processes the data acquired, and outputs an image to display 1008. It should be noted that the computer 1002, physiological control system 1004, data acquisition system 1006 and display 1008 may be integrated into a single unit, into fewer components, etc.

Computer 1002 typically includes at least some form of computer readable media. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory, or other memory technology, CD-ROM, digital versatile disks (DVD) or other optical storage, magnetic cassettes, magnetic tape, magnetic disk storage or other magnetic storage devices, or any other medium which can be used to store the desired information. Communication media typically embodies computer readable instructions, data structures, program modules, or other data in a modulated data signal such as a carrier wave or other transport mechanism and includes any information delivery media.

It can be seen from the foregoing that a cardiac adaptive diastolic interval (ADI) control algorithm that attempts to restore a period-1 rhythm to a tissue exhibiting a pathologic higher-period or aperiodic rhythm has been presented. This method does not require any knowledge or estimation (either before or during control) of the fixed-point dynamics, can be used to control both periodic and aperiodic rhythms to the period-1 rhythm, and is robust to drift and noise. The ADI control of the invention presents an alternative method for controlling both periodic and aperiodic rhythm disturbances. ADI control was tested on a variety of models exhibiting an array of characteristic behaviors, as each model alone is an imperfect approximation to real cardiac myocytes. These simulations indicate that the ADI control algorithm may be therapeutically preferable to existing control strategies, as control rapidly converges to the period-1 rhythm over at least as wide, and in some cases wider, range of feedback parameter values compared to existing DFC algorithms. When applied to real cardiac tissue, it is possible that the ranges of feedback parameter values over which DFC and ADI control succeed may be quantitatively different from the ranges obtained in our simulations. If that is the case, the control algorithm has to guess the value of the feedback parameter value prior to control initiation. Our simulations suggest that the feedback parameter regime resulting in control success may be larger in some situations with ADI control than with restricted DFC. Therefore, an initial estimate for the feedback parameter value should more likely lead to control success with ADI control than with DFC.

In the foregoing description, ADI control was initiated only when the inequality $DI_n + APD_{n+1} < BCL$ was satisfied. This inequality assumes that it is not possible to excite the tissue at a rate slower than some intrinsic systemic rate. This condition ensures that each subsequent DI is lengthened until the original cycle length is reached, provided a small enough value of the proportionality constant $\alpha$ is chosen.

Such unidirectional perturbations constitute a restricted form of ADI control. However, if bidirectional perturbations to the cycle length are possible, unrestricted ADI control may be initiated at any time, as both shortening and lengthening of the cycle length are allowed with the same control algorithm (as shown in FIGS. 6a and 6b). For example, the adjustment of DI could be rewritten as $DI_{n+1}=DI_n-\alpha[BCL_n-BCL^*]$ when $BCL_n>BCL^*$ or it could remain the same as before ($DI_{n+1}=DI_n+\alpha[BCL^*-BCL_n]$) when $BCL_n>BCL^*$.

ADI control is somewhat similar to the "demand pacing" approach in which the heart is stimulated at a particular BCL if it has not yet spontaneously beat. However, ADI control is fundamentally different in that it initiates pacing not at a constant BCL but at a constant DI. Thus, while demand pacing at any BCL within the APD alternans regime causes (rather than eliminates) alternans, ADI control eliminates alternans by adaptively changing the BCL on a beat-to-beat basis.

The ADI control methodology of the invention use information about the system (e.g., APD and DI) only from the control site to make decisions about when to apply the next stimulus. Improved control may be possible by utilizing information about the dynamics occurring some distance away from the control site. Similarly, applying local control to many positions in a tissue may present a way of improving spatiotemporal control of electrophysiological rhythm disturbances.

It is to be understood that while the present invention has been described above in conjunction with preferred specific embodiments, the description is intended to illustrate and not to limit the scope of the invention, as defined by the appended claims. Indeed, various modifications of the invention in addition to those described herein will become apparent to those skilled in the art from the foregoing description and the accompanying figures. Such modifications are intended to fall within the scope of the appended claims. It is further to be understood that all values are to some degree approximate, and are provided for purposes of description.

What is claimed is:

1. A method to reduce a non-period-1 action potential duration rhythm to a period-1 action potential duration rhythm comprising the steps of:
    determining a diastolic interval of a first action potential pulse;
    determining an end of a second action potential pulse occurring after the end of the diastolic interval of the first action potential pulse; and
    providing a stimulation so as to initiate a third action potential pulse at a time interval after the end of the second action potential pulse, the time interval being substantially equal to the diastolic interval of the first action potential pulse and determined without regard to a period-1 fixed point rhythm prior to the first action potential pulse.

2. The method of claim 1, comprising:
    providing a stimulation so as to initiate a further action potential pulse at a further time interval after the end of a previous action potential pulse, the further time interval being substantially equal to a diastolic interval preceding the previous action potential pulse adjusted by a correction interval.

3. The method of claim 2, wherein the correction interval is a function of the difference between a basic cycle length and a sum of the diastolic interval preceding the previous action potential pulse and a duration of the previous action potential pulse.

4. The method of claim 3, wherein the correction interval is equal to a fraction of the sum, the fraction having a value between 0 and 1.

5. A method to reduce a non-period-1 action potential duration rhythm occurring at an original basic cycle length (BCL*) to a period-1 action potential duration rhythm comprising the steps of:
    selecting an initial target diastolic interval (DI) substantially equal to a diastolic interval of a first action potential pulse;
    applying a control perturbation so as to initiate an action potential pulse at a time interval after the end of a previous action potential pulse occurring after the end of the diastolic interval of the first action potential pulse, the time interval being substantially equal to The target DI and determined without regard to a period-1 fixed point rhythm prior to the first action potential pulse; and
    adaptively changing the target DI on a beat-to-beat basis such that a difference between the present cycle length and the original basic cycle length is reduced.

6. The method of claim 5 wherein the step of adaptively changing the target DI comprises the step of adjusting the target DI according to the equation $$DI_{n+1}=DI_n 30\ \alpha[BCL^*-BCL_n]$$

where $DI_{n+1}$ is the next target diastolic interval, $DI_n$ is the present target diastolic interval, $\alpha$ is a constant greater than or equal to zero that controls the rate at which $DI_n$ changes, and $BCL_n$ is the present basic cycle length.

7. The method of claim 6 wherein $\alpha$ has a value between 0 and 1.

8. The method of claim 5 wherein the step of adaptively changing the target DI comprises the step of adjusting the target DI according to the equation $$DI_{n+1}=DI_n 31\ \alpha[BCL_n-BCL^*]$$

where $DI_{n+1}$ is the next target diastolic interval, $DI_n$ is the present target diastolic interval, $\alpha$ is a constant greater than or equal to zero that controls the rate at which $DI_n$ changes, and $BCL_n$ is the present basic cycle length.

9. The method of claim 5 wherein the step of adaptively changing the target DI on a beat-to-beat basis such that a difference between the present cycle length and the original basic cycle length is reduced comprises the step of adaptively changing the target DI on a beat-to-beat basis such that a difference between the present cycle length and the original basic cycle length is approximately zero.

10. A computer-readable medium having computer-executable instructions for reducing a non-period-1 action potential duration rhythm occurring at an original basic cycle length (BCL*) to a period-1 action potential duration rhythm, the computer-executable instructions for performing the steps of:
    selecting an initial target diastolic interval (DI) substantially equal to a diastolic interval of a first action potential pulse;
    applying a control perturbation so as to initiate an action potential pulse at a time interval after the end of a previous action potential pulse occurring after the end of the diastolic interval of the first action potential pulse, the time interval being substantially equal to the target DI and determined without regard to a period-1 fixed point rhythm prior to the first action potential pulse.

adaptively changing the target DI on a beat-to-beat basis such that a difference between the present cycle length and the original basic cycle length is reduced.

11. The computer-readable medium of claim 10 wherein the step of adaptively changing the target DI comprises the step of adjusting the target DI according to the equation $$DI_{n+1} = DI_n + \alpha[BCL^* - BCL_n]$$

where $DI_{n+1}$ is the next target diastolic interval, $DI_n$ is the present target diastolic interval, $\alpha$ is a constant greater than or equal to zero that controls the rate at which $DI_n$ changes, and $BCL_n$ is the present basic cycle length.

12. The computer-readable medium of claim 11 wherein $\alpha$ has a value between 0 and 1.

13. The computer-readable medium of claim 10 wherein the step of adaptively changing the target DI comprises the step of adjusting the target DI according to the equation $$DI_{n+1} = DI_n - \alpha[BCL_n - BCL^*]$$

where $DI_{n+1}$ is the next target diastolic interval, $DI_n$ is The present target diastolic interval, $\alpha$ is a constant greater than or equal to zero that controls the rate at which $DI_n$ changes, and $BCL_n$ is the present basic cycle length.

14. The computer-readable medium of claim 10 wherein the step of adaptively changing The target DI on a beat-to-beat basis such that a difference between the present cycle length and the original basic cycle length is reduced comprises the step of adaptively changing the target DI on a beat-to-beat basis such that a difference between the present cycle length and the original basic cycle length is approximately zero.

15. The computer-readable medium of claim 10 wherein the step of selecting an initial target diastolic interval comprises the step of determining the diastolic interval of the first action potential pulse.

16. The computer-readable medium of claim 15 wherein the step of adaptively changing the target DI on a beat-to-beat basis such that a difference between the present cycle length and The original basic cycle length is reduced includes the steps of:
  determining an end of a second action potential pulse; and
  providing a stimulation so as to initiate a third action potential pulse at a time interval after the end of the second action potential pulse, the time interval being substantially equal to the diastolic interval of the first action potential pulse.

17. The computer-readable medium of claim 16, comprising:
  providing a stimulation so as to initiate a further action potential pulse at a further time interval after the end of a previous action potential pulse, the further time interval being substantially equal to a diastolic interval preceding the previous action potential pulse adjusted by a correction interval.

18. The computer-readable medium of claim 17, wherein the correction interval is a function of the difference between a basic cycle length and a sum of the diastolic interval preceding the previous action potential pulse and a duration of the previous action potential pulse.

19. The computer-readable medium of claim 18 wherein the correction interval is equal to a fraction of the sum, the fraction having a value between 0 and 1.

* * * * *